US009924935B2

(12) United States Patent
Housman

(10) Patent No.: US 9,924,935 B2
(45) Date of Patent: Mar. 27, 2018

(54) SUTURE ANCHOR ASSEMBLY WITH SLIP FIT TIP

(71) Applicant: Smith & Nephew, Inc., Memphis, TN (US)

(72) Inventor: Mark Edwin Housman, North Attleborough, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/238,133

(22) Filed: Aug. 16, 2016

(65) Prior Publication Data

US 2017/0112485 A1   Apr. 27, 2017

Related U.S. Application Data

(60) Provisional application No. 62/245,307, filed on Oct. 23, 2015.

(51) Int. Cl.
*A61B 17/04* (2006.01)
*A61B 17/00* (2006.01)

(52) U.S. Cl.
CPC ............. *A61B 17/0401* (2013.01); *A61B 2017/00004* (2013.01); *A61B 2017/0403* (2013.01); *A61B 2017/0409* (2013.01); *A61B 2017/0412* (2013.01); *A61B 2017/0414* (2013.01); *A61B 2017/0445* (2013.01); *A61B 2017/0453* (2013.01); *A61B 2017/0456* (2013.01); *A61B 2017/0458* (2013.01)

(58) Field of Classification Search
CPC ...... A61B 17/0401; A61B 2017/00004; A61B 2017/0403; A61B 2017/0453; A61B 2017/0456; A61B 2017/0414; A61B 2017/0445; A61B 2017/0409

USPC ........................................................ 606/232
See application file for complete search history.

(56) References Cited

U.S. PATENT DOCUMENTS

| 3,187,620 A | 6/1965 | Fischer |
| 3,268,965 A | 8/1966 | Read |
| 4,636,121 A | 1/1987 | Miller |
| 4,750,492 A | 6/1988 | Jacobs |
| 4,870,957 A | 10/1989 | Somers |
| 4,927,421 A | 5/1990 | Somers |
| 5,037,422 A | 8/1991 | Hayhurst |
| 5,100,417 A | 3/1992 | Warren |
| 5,102,421 A | 4/1992 | Anspach, Jr. |
| 5,141,520 A | 8/1992 | Somers |
| 5,152,790 A | 10/1992 | Carlozzi |
| 5,156,616 A | 10/1992 | Ogden |
| 5,176,682 A | 1/1993 | Chow |

(Continued)

FOREIGN PATENT DOCUMENTS

| WO | 2012140427 A1 | 10/2012 |
| WO | 2015005951 A1 | 1/2015 |

OTHER PUBLICATIONS

International Search Report and Written Opinion from related PCT Application No. PCT/US2016/048048 dated Oct. 17, 2016.

*Primary Examiner* — Diane Yabut
*Assistant Examiner* — Erich Herbermann
(74) *Attorney, Agent, or Firm* — Norman F. Hainer, Jr.

(57) ABSTRACT

A suture anchor assembly including a suture anchor that incorporates a harder distal tip with a softer proximal body. The tip and body of the suture anchor are connected via a threaded plug, which also serves to connect the suture anchor to an inserter.

17 Claims, 5 Drawing Sheets

(56) References Cited

U.S. PATENT DOCUMENTS

| | | |
|---|---|---|
| 5,258,016 A | 11/1993 | Small |
| 5,268,001 A | 12/1993 | Hart |
| 5,356,435 A | 10/1994 | Thein |
| 5,370,662 A | 12/1994 | Stone |
| 5,376,119 A | 12/1994 | Zimmermann et al. |
| 5,383,905 A | 1/1995 | Golds |
| 5,423,860 A | 6/1995 | Lizardi |
| 5,458,601 A | 10/1995 | An |
| 5,464,427 A | 11/1995 | Schlegel |
| 5,480,403 A | 1/1996 | Lee |
| 5,486,197 A | 1/1996 | Luscombe |
| 5,500,000 A | 3/1996 | Feagin |
| 5,500,843 A | 3/1996 | Ishii |
| 5,505,735 A | 4/1996 | Li |
| 5,522,843 A | 6/1996 | Zang |
| 5,527,342 A | 6/1996 | Wiley |
| 5,545,180 A | 8/1996 | Yi |
| 5,584,835 A | 12/1996 | Greenfield |
| 5,584,860 A | 12/1996 | Perakis |
| 5,607,432 A | 3/1997 | Fucci |
| 5,630,824 A | 5/1997 | Hart |
| 5,690,676 A | 11/1997 | DiPoto |
| 5,702,397 A | 12/1997 | Luman |
| 5,707,395 A | 1/1998 | Li |
| 5,720,765 A | 2/1998 | Thal |
| 5,723,013 A | 3/1998 | Marnay |
| 5,725,529 A | 3/1998 | Nicholson |
| 5,728,136 A | 3/1998 | Thal |
| 5,733,307 A | 3/1998 | Dinsdale |
| 5,797,963 A | 8/1998 | McDevitt |
| 5,827,291 A | 10/1998 | Trott |
| 5,849,004 A | 12/1998 | Bramlet |
| 5,911,721 A | 6/1999 | Nicholson |
| RE36,289 E | 8/1999 | Le et al. |
| 5,935,129 A | 8/1999 | McDevitt |
| 5,948,000 A | 9/1999 | Larsen et al. |
| 5,948,001 A | 9/1999 | Larsen |
| 5,957,953 A * | 9/1999 | DiPoto ............... A61B 17/0401 606/232 |
| 5,978,000 A | 11/1999 | Levine |
| 6,010,525 A | 1/2000 | Bonutti |
| 6,086,608 A | 7/2000 | Ek et al. |
| 6,117,162 A | 9/2000 | Grafton |
| 6,129,763 A | 10/2000 | Attia |
| 6,136,032 A | 10/2000 | Viladot Perice |
| 6,136,062 A | 10/2000 | Loffelholz |
| 6,146,387 A | 11/2000 | Trott |
| 6,149,669 A | 11/2000 | Li |
| 6,152,934 A | 11/2000 | Harper et al. |
| 6,159,235 A | 12/2000 | Kim |
| 6,165,203 A | 12/2000 | Krebs |
| 6,200,329 B1 | 3/2001 | Ek |
| 6,200,330 B1 | 3/2001 | Ryan |
| 6,206,886 B1 | 3/2001 | Bennett |
| 6,214,007 B1 | 4/2001 | Anderson |
| 6,228,096 B1 | 5/2001 | Marchand |
| 6,267,766 B1 | 7/2001 | Burkhart |
| 6,287,324 B1 | 9/2001 | Kahana |
| 6,319,271 B1 | 11/2001 | Fromm |
| 6,368,326 B1 | 4/2002 | Lippincott III |
| 6,436,124 B1 | 8/2002 | Pirhonen |
| 6,436,142 B1 | 8/2002 | Paes |
| 6,517,542 B1 | 2/2003 | Byerman |
| 6,520,980 B1 | 2/2003 | Foerster |
| 6,527,794 B1 | 3/2003 | Halbrecht |
| 6,533,816 B2 | 3/2003 | Sklar |
| 6,575,987 B2 | 6/2003 | Brenneman |
| 6,585,730 B1 | 7/2003 | Foerster |
| 6,616,694 B1 | 9/2003 | Hart |
| 6,641,596 B1 | 11/2003 | Lizardi |
| 6,652,563 B2 | 11/2003 | Dreyfuss |
| 6,692,516 B2 | 2/2004 | West, Jr. |
| 6,726,707 B2 | 4/2004 | Pedlick et al. |
| 6,736,829 B1 | 5/2004 | Li |
| 6,783,527 B2 | 8/2004 | Molz |
| 6,840,953 B2 | 1/2005 | Martinek |
| 7,008,451 B2 | 3/2006 | Wenstrom, Jr. |
| 7,083,638 B2 | 8/2006 | Foerster |
| 7,090,690 B2 | 8/2006 | Foerster |
| 7,381,213 B2 | 6/2008 | Lizardi |
| 7,416,556 B2 | 8/2008 | Jackson |
| 7,491,217 B1 | 2/2009 | Putnam |
| 7,517,357 B2 | 4/2009 | Keegan |
| 7,585,311 B2 | 9/2009 | Bojanowski |
| 7,604,640 B2 | 10/2009 | Kana |
| 7,867,264 B2 | 1/2011 | McDevitt et al. |
| 7,938,847 B2 | 5/2011 | Krumme |
| 8,118,635 B2 | 2/2012 | Weisel et al. |
| 8,118,835 B2 | 2/2012 | Weisel |
| 8,133,258 B2 | 3/2012 | Gordon |
| 8,137,381 B2 | 3/2012 | Aldridge |
| 8,162,978 B2 | 4/2012 | Fitts |
| 8,777,990 B2 | 7/2014 | van der Burg et al. |
| 8,948,001 B2 | 2/2015 | Ward |
| 8,986,345 B2 | 3/2015 | Denham et al. |
| 2001/0000707 A1 | 5/2001 | Kikinis |
| 2001/0007072 A1 | 7/2001 | Steiner |
| 2002/0058966 A1 | 5/2002 | Tormala |
| 2002/0088301 A1 | 7/2002 | Amery |
| 2002/0147463 A1 | 10/2002 | Martinek |
| 2002/0161401 A1 | 10/2002 | Steiner |
| 2002/0188301 A1 | 12/2002 | Amery |
| 2003/0065361 A1 | 4/2003 | Dreyfuss |
| 2003/0065390 A1 | 4/2003 | Wenstrom |
| 2003/0033669 A1 | 5/2003 | Gleason |
| 2003/0083669 A1 | 5/2003 | Gleason |
| 2003/0088272 A1 | 5/2003 | Smith |
| 2003/0137446 A1 | 10/2003 | Overaker |
| 2003/0187446 A1 | 10/2003 | Overaker |
| 2003/0195563 A1 | 10/2003 | Foerster |
| 2003/0208210 A1 | 11/2003 | Romeo |
| 2004/0038050 A1 | 2/2004 | Saijo |
| 2004/0062506 A1 | 4/2004 | Hosokawa |
| 2004/0088004 A1 | 5/2004 | Rosch |
| 2004/0093031 A1 | 5/2004 | Elattrache |
| 2004/0096080 A1 | 5/2004 | Peng |
| 2004/0098050 A1 | 5/2004 | Foerster et al. |
| 2004/0098052 A1 | 5/2004 | West |
| 2004/0133239 A1 | 7/2004 | Singhatat |
| 2004/0138706 A1 | 7/2004 | Reimels |
| 2004/0138707 A1 | 7/2004 | Greenhalgh |
| 2004/0225313 A1 | 11/2004 | Kanner |
| 2005/0033364 A1 | 2/2005 | Gregoire |
| 2005/0055052 A1 | 3/2005 | Amery |
| 2005/0107828 A1 | 5/2005 | Reese |
| 2005/0216015 A1 | 9/2005 | Kreidler |
| 2005/0222618 A1 | 10/2005 | Dreyfuss |
| 2005/0245932 A1 | 11/2005 | Ashley |
| 2006/0004364 A1 | 1/2006 | Bojanowski |
| 2006/0058800 A1 | 3/2006 | Assell |
| 2006/0079904 A1 | 4/2006 | Thal |
| 2006/0235413 A1 | 10/2006 | Denham |
| 2006/0247642 A1 | 11/2006 | Stone et al. |
| 2006/0253119 A1 | 11/2006 | Berberich |
| 2006/0271060 A1 | 11/2006 | Gordon |
| 2006/0282081 A1 | 12/2006 | Krumme |
| 2007/0005068 A1 | 1/2007 | Sklar |
| 2007/0005069 A1 | 1/2007 | Contiliano |
| 2007/0038219 A1 | 2/2007 | Biedermann |
| 2007/0142835 A1 | 6/2007 | Greelis |
| 2007/0167950 A1 | 7/2007 | Tate |
| 2007/0203498 A1 | 8/2007 | Berberich |
| 2007/0218424 A1 | 9/2007 | Nurmi |
| 2007/0225736 A1 | 9/2007 | Ortiz |
| 2007/0288023 A1 | 12/2007 | Pellegrino |
| 2008/0009904 A1 | 1/2008 | Bourque |
| 2008/0015594 A1 | 1/2008 | Foerster |
| 2008/0033460 A1 | 2/2008 | Ziniti |
| 2008/0051836 A1 | 2/2008 | Vijay |
| 2008/0077161 A1 | 3/2008 | Kaplan |
| 2008/0125815 A1 | 5/2008 | Heaven |
| 2008/0133007 A1 | 6/2008 | Cauldwell |
| 2008/0208253 A1 | 8/2008 | Sodeika |
| 2008/0215061 A1 | 9/2008 | Kramer |

(56) References Cited

U.S. PATENT DOCUMENTS

| | | |
|---|---|---|
| 2008/0231353 A1 | 9/2008 | Aranyi |
| 2008/0249567 A1 | 10/2008 | Kaplan |
| 2008/0281353 A1 | 11/2008 | Aranyi |
| 2009/0112270 A1* | 4/2009 | Lunn ............... A61B 17/0401 606/301 |
| 2009/0157124 A1 | 6/2009 | Ferragamo et al. |
| 2009/0312794 A1 | 12/2009 | Hoof |
| 2009/0318965 A1 | 12/2009 | Burkhart |
| 2009/0326545 A1 | 12/2009 | Schaffhausen |
| 2010/0004683 A1 | 1/2010 | Hoof |
| 2010/0016869 A1 | 1/2010 | Paulk et al. |
| 2010/0016902 A1 | 1/2010 | Paulk et al. |
| 2010/0094355 A1 | 4/2010 | Trenhaile |
| 2010/0318125 A1 | 12/2010 | Berberich |
| 2011/0112576 A1* | 5/2011 | Nguyen ............ A61B 17/0401 606/232 |
| 2012/0083840 A1 | 4/2012 | DiMatteo et al. |
| 2012/0296345 A1 | 11/2012 | Wack et al. |
| 2013/0006302 A1* | 1/2013 | Paulk ............... A61B 17/0401 606/232 |
| 2013/0204298 A1 | 8/2013 | Graul et al. |
| 2013/0267998 A1* | 10/2013 | Vijay ............... A61B 17/0401 606/232 |
| 2014/0066982 A1* | 3/2014 | Stone ............... A61B 17/0401 606/232 |
| 2014/0222072 A1 | 8/2014 | Gerber et al. |
| 2014/0257385 A1 | 9/2014 | Lunn et al. |
| 2014/0277128 A1 | 9/2014 | Moore et al. |
| 2014/0277129 A1* | 9/2014 | Arai ................. A61B 17/0401 606/232 |
| 2014/0277219 A1 | 9/2014 | Nanda |
| 2014/0364906 A1 | 12/2014 | Palese et al. |
| 2015/0012015 A1 | 1/2015 | Berelsman et al. |

* cited by examiner

SUTURE ANCHOR ASSEMBLY WITH SLIP FIT TIP

CROSS-REFERENCE TO RELATED APPLICATIONS

This application claims priority to and benefit of U.S. Provisional Application No. 62/245,307, filed Oct. 23, 2015, entitled SUTURE ANCHOR ASSEMBLY WITH SLIP FIT TIP, the contents of which are incorporated herein by reference in their entirety for all purposes.

TECHNICAL FIELD

This present disclosure relates to a suture anchor assembly and, more particularly, to a suture anchor assembly having a slip fit tip.

BACKGROUND

Arthroscopy surgery is a minimally-invasive surgery that involves the repair of tissue inside or around a joint. In shoulder arthroscopy, for example, common injuries include a torn or damaged cartilage ring or ligaments (causing shoulder instability), a torn rotator cuff, or a torn or damaged biceps tendon. Each of these injuries necessitates the reattachment of soft tissue (that is, the ligaments or tendons) to bone. Current methods of arthroscopic fixation of soft tissues to bone involve the placement of suture anchors in bone, and reducing tissue to bone by passing a suture through the tissue and tying surgical knots to secure the tissue against the bone.

In the construction of suture anchors, it is often desirable for the anchor to be made of different materials. For example, a harder (typically metal) tip, is useful for driving the anchor into bone, while a softer (typically polymer) main body can be reabsorbed into the body over time. However, constructing a suture anchor from different materials presents difficulties in connecting the tip to the body. Current methods for connecting a metal tip with a polymer main body are by over-molding of the parts, or the use of a stay suture. However, both of these methods add costs to manufacturing the suture anchor and may lead to unreliability in the surgical procedure.

SUMMARY

Described herein is a suture anchor that incorporates a harder distal tip with a softer proximal body without the need for connection by over-molding the parts or the use of a stay suture. Advantageously, the tip and body of the suture anchor do not move axially with respect to each other, nor are they rigidly connected. Instead, tip and body are connected via a threaded plug, which also serves to connect the suture anchor to an inserter. Advantageously, such simplified manufacturing leads both to lower cost of manufacturing and to higher reliability during surgical use.

In examples, the suture anchor assembly includes an anchor having a tip, the tip including a proximal end and a tapered distal end, a longitudinal axis extending between the proximal and distal ends. An eyelet extends transversely through the longitudinal axis of the tip and is dimensioned to receive one or more sutures. A cannulation is formed within the tip in communication with the eyelet. The cannulation has threads which extend from the proximal end of the cannulation to a region proximal to the distal end of the eyelet. The anchor also has an elongated anchor body formed separately from the tip. The anchor body includes an open cannula extending from a proximal end to a distal end, the distal end of the cannula dimensioned to receive the proximal end of the tip. The anchor further includes a threaded plug formed separately from both the anchor body and the tip, the plug configured to engage the cannulation of the tip. The suture anchor assembly also includes an inserter having an outer shaft dimensioned for receipt within the cannula of the anchor body and an inner shaft dimensioned for receipt within the outer shaft, the inner shaft being axially and rotationally moveable independent of the outer shaft. An inner surface of the outer shaft comprises threads engageable with the threads of the plug.

In other examples, the tip is made of a material selected be harder than the material of the anchor body, which may be one of plastic, titanium and stainless steel. The anchor body is made of bioabsorbable material. A transverse anchor body eyelet is located on the anchor body such that, when the proximal end of the tip is inserted into the distal end of the cannula of the anchor body, the tip eyelet and the anchor body eyelet are aligned. The inner shaft of the inserter is configured for insertion into the plug. The anchor body is trapped axially between the inserter and the tip when the threaded plug is engaged with the threaded cannulation of the outer shaft of the inserter and the threaded cannulation of the tip. The interface between the inserter and the anchor body, as well as between the anchor body and the tip, is a slip fit. The assembly may also include a suture extending transversely through the tip eyelet and the anchor body eyelet.

In further examples, the plug is made of one of a polymer, a plastic and a metal. A diameter of the plug may be about 2 mm, and a length of the plug may be about 5.25 mm. The anchor body comprises surface features to aid in the retention in bone. The inner shaft of the inserter defines a taper between a round proximal portion and a polygonal distal portion, which may be triangular.

An example of the method of fixing soft tissue to bone of this disclosure may include: a) passing a suture through a suture anchor assembly as described above; and b) axially and rotationally descending the plug within the cannulation of the tip, thus trapping the suture between the distal end of the plug and a distal end of the cannulation of the tip. Axially and rotationally descending the plug within the cannulation of the tip includes using a portion of an inserter to axially and rotationally descend the plug within the cannulation of the tip. The method may further include, after step a), fully hammering the suture anchor assembly into bone and, after step b), removing the inserter from the suture anchor assembly.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
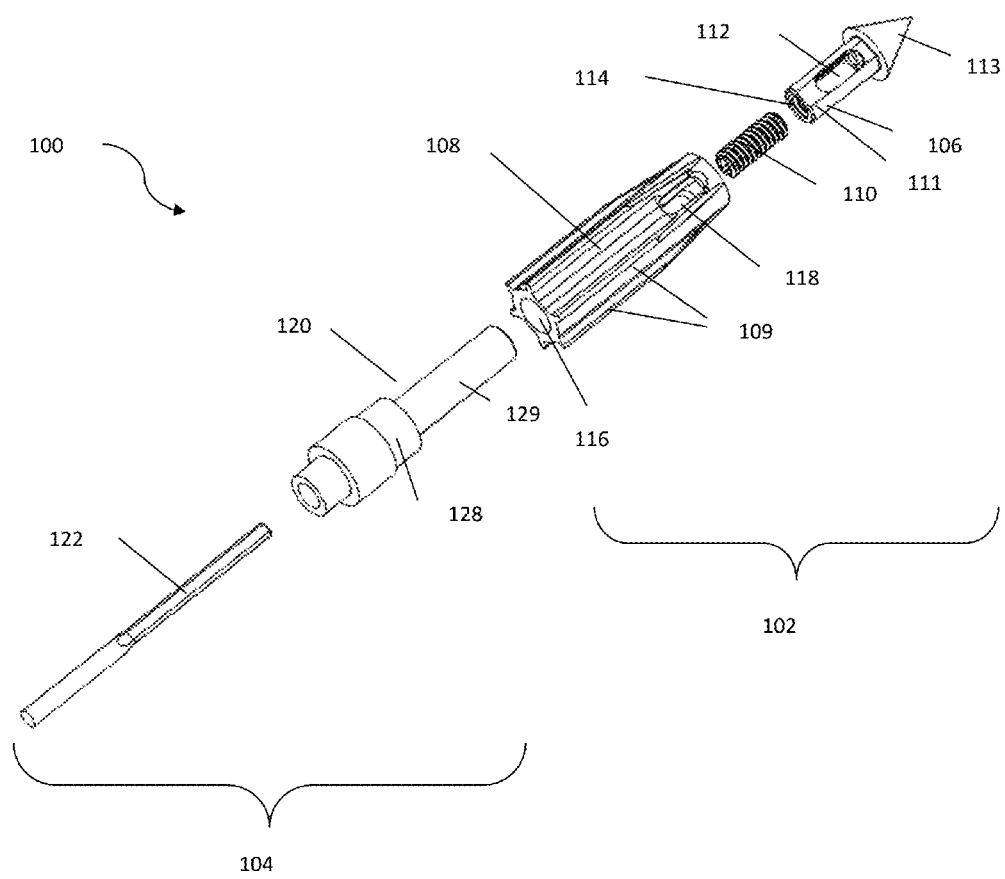
FIG. 1A is an exploded view of an exemplary suture anchor assembly of this disclosure.

Examples of the suture anchor assembly and methods of use will now be discussed with reference to the figures.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Comprise, include, and/or plural forms of each are open ended and include the listed parts and can include additional parts that are not listed. And/or is open ended and includes one or more of the listed parts and combinations of the listed parts.

Referring now to FIG. 1A, an example of a suture anchor assembly 100 of this disclosure is illustrated. The suture anchor assembly 100 generally includes an anchor 102 and an inserter 104. The anchor 102 further comprises a tip 106, an elongated anchor body 108 formed separately from the tip 106, and a hollow, threaded plug 110. As described further below, when assembled, the plug 110 connects the tip 106 to the anchor body 108.

The tip 106 has a generally cylindrical proximal portion 111 and a tapered distal portion 113. A widest dimension of the tapered distal portion 113 is selected to be larger than the circumference of the cylindrical proximal portion 111. The distalmost end of the tapered distal portion 113 may be pointed to aid in insertion in bone. The tip 106 is comprised of a material, such as plastic, titanium or stainless steel, selected to be harder than the material of the anchor body 108. A tip eyelet 112 extends transversely through the cylindrical proximal portion 111 of the tip 106 and is dimensioned to receive one or more flexible elements, such as sutures. The tip 106 also includes a cannulation 114 in communication with the tip eyelet 112 and having inner threads extending from the proximal end of the cannulation 114 to a region proximal to the distal end of the tip eyelet 112.

The plug 110 is formed separately from both the anchor body 108 and the tip 106. The plug 110 is sized to engage the threaded cannulation 114 of the tip 106. The interior of the plug 110 is configured to receive a portion of the inserter 104, as described further below. The diameter of the plug 110 may be about 2 mm and the length may be about 5.25 mm. The plug 110 may be comprised of any suitable material, such as polymers, plastics or metals.

Still referring to FIG. 1A, the anchor body 108 comprises an open cannula 116 extending the length of the anchor body 108. The distal end of the cannula 116 is dimensioned to receive the cylindrical proximal portion 111 of the tip 106. The distal end of the anchor body 108 also includes a transverse anchor body eyelet 118 dimensioned to receive one or more sutures. The anchor body eyelet 118 is located on the anchor body 108 in a position such that, when the cylindrical proximal portion 111 of the tip 106 is inserted into the anchor body 108, the tip eyelet 112 and the anchor body eyelet 118 are aligned, as further described below. In FIG. 1A, the surface of the anchor body 108 is shown as comprising longitudinal ribs 109 to aid in retention within bone. However, other surface features, such helical ribs or barbs, are also contemplated by this disclosure.

The anchor body 108 can be made from any combination of metal, bioabsorbable, or biocomposite material. For example, the anchor body 108 may be partially or entirely formed from a formulation of poly(lactic-co-glycolic) acid (PLGA), β-Tricalcium phosphate (β-TCP) and calcium sulfate, poly-L-lactic acid-hydroxyapatite (PLLA-HA), poly (PDLA), polymers such as polyether ether ketone (PEEK), or variants thereof. Biocomposite examples made from a combination of PLGA, β-TCP, and calcium sulfate are absorbable by the body, which is beneficial to natural healing. An example formulation of PLGA, β-TCP, and calcium sulfate is described in U.S. Pat. No. 8,545,866, the entirety of which is herein incorporated by reference. A copolymer of polyglycolic acid (PGA) and polytrimethylene carbonate (TMC) is another example of a bioabsorbable material. Other commonly used materials that are capable of providing the strength needed to set the anchor body 108 and to hold the tissue graft in position while bone-to-tissue in-growth occurs are also contemplated by this disclosure.

Still referring to FIG. 1A, the inserter 104 of the suture anchor assembly 100 includes a handle (not shown) having a hollow outer shaft 120 extending from the handle. An inner shaft 122 is disposed within the outer shaft 120, and is attached to a rotational member of the handle, such as a knob (not shown), such that the inner shaft 122 is both axially and rotationally movable independent of the outer shaft 120 by turning the knob. The outer shaft 120 includes a proximal shelf portion 128 and a distal insertion portion 129, the purpose of which will be further described below. A diameter of the proximal shelf portion 128 is selected to be larger than a diameter of the distal insertion portion 129, which in turn is dimensioned for receipt within the cannula 116 of the anchor body 108.

Figure 1B:
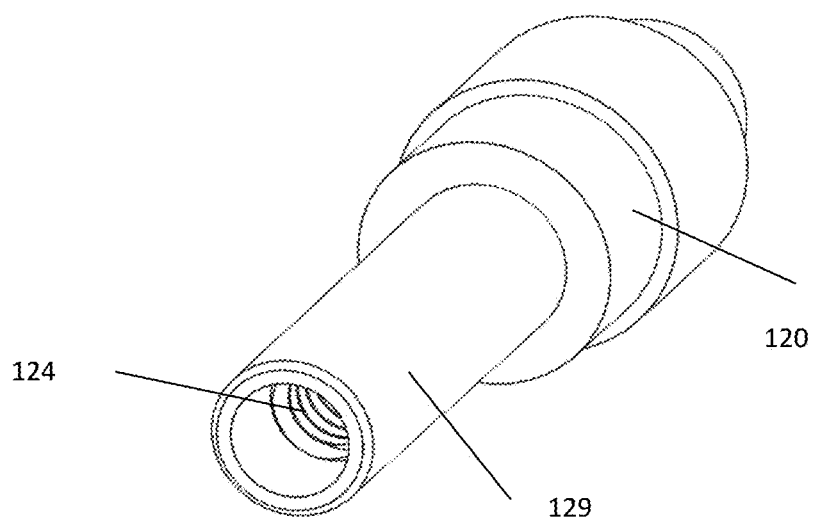
FIG. 1B is a detailed view of the inserter of FIG. 1A.

FIG. 1B shows a detailed view of the outer shaft 120. Here, it can be seen that the distalmost portion of the cannulation 124 of the outer shaft 120 is non-threaded while an inner portion comprises threads. The threads are engageable with the threads of the plug 110, as further described below.

Figure 2:
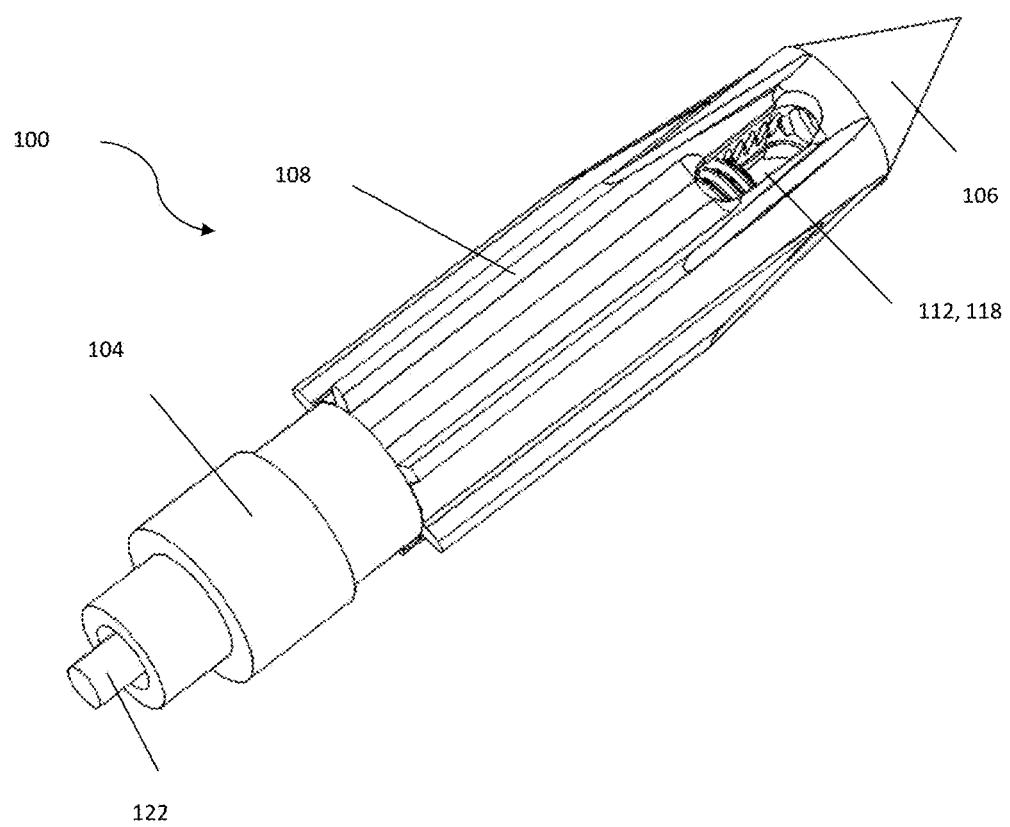
FIG. 2 is an assembled view of the suture anchor assembly of FIG. 1A.

FIG. 2 illustrates an assembled view of the suture anchor assembly 100 of FIG. 1A. In FIG. 2, it can be seen that the anchor body 108 is trapped axially between the inserter 104 and the tip 106. The interface between the inserter 104 and the anchor body 108 is shown as a slip fit, as is the interface between the anchor body 108 and the tip 106. However, it is contemplated by this disclosure that the interface between the anchor body 108 and the tip 106 could be also a press (interference) fit. Advantageously, this arrangement limits axial movement between the anchor body 108 and the tip 106, without the need for the anchor body 108 and the tip 106 to be rigidly connected to one other. Furthermore, since both the tip eyelet 112 and the anchor body eyelet 118 are aligned, a suture or other suitable flexible material may easily be loaded into the suture anchor assembly 100.

Figure 3A:
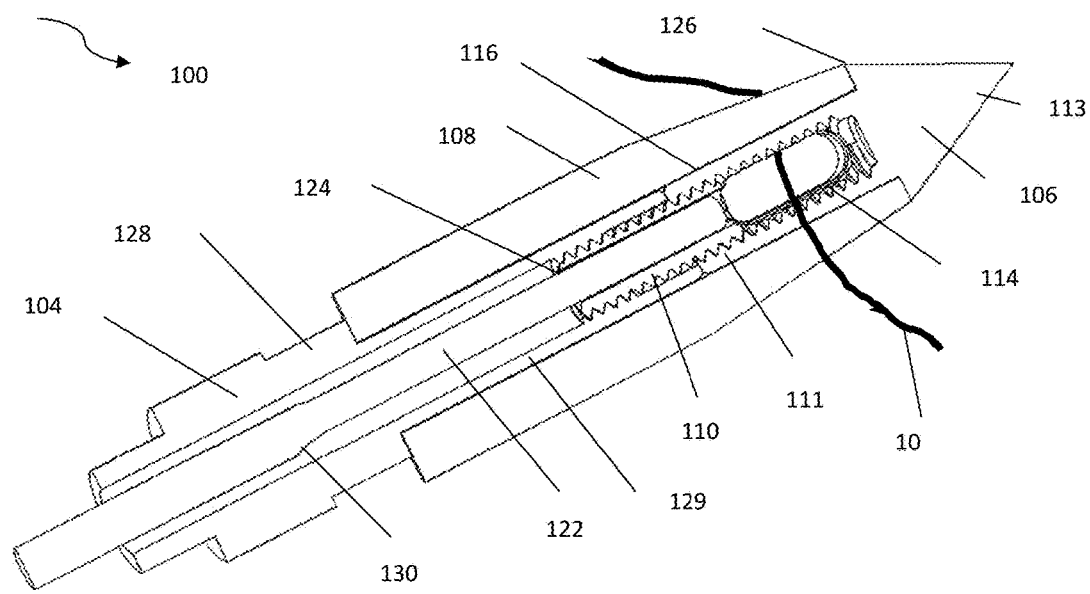
FIGS. 3A-B are cross-sectional views of a method of using the suture anchor assembly of FIG. 1A.
Figure 3B:
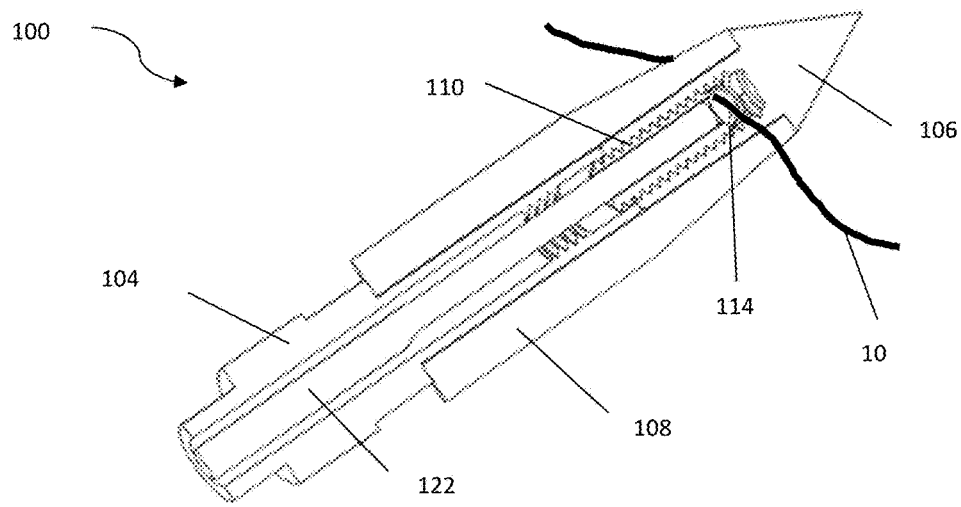

FIGS. 3A-B illustrate a method of use of the suture anchor assembly 100 of FIG. 1A. In examples, the suture anchor assembly 100 could be used for instability (labral) repair of the shoulder. However, it is also contemplated by this disclosure that the suture anchor assembly 100 could be adapted or scaled for other types of arthroscopic surgical repair.

FIG. 3A shows a cross-section of the assembled suture anchor assembly 100 of FIG. 2. The tip 106 and the inserter 104 are connected to each other via the external threads on the plug 110 which mate with both the internal threads of the cannulation 114 of the tip 106, as well as the internal threads of the outer shaft cannulation 124 of the inserter 104. The insertion portion 129 of the inserter 104 is shown as inserted into the open cannula 116 of the anchor body 108 until it abuts the cylindrical proximal portion 111 of the tip 106. The tip 106 defines a tip shelf 126 at the widest part of the tapered distal portion 113. Thus, the anchor body 108 is axially trapped between the tip shelf 126 and the shelf portion 128 of the inserter 104.

Still referring to FIG. 3A, the anchor body 108 is shown as having a cylindrical body slightly tapering toward the tip 106, but other shapes are possible as long as they are selected to wedge the anchor body 108 between the tip shelf 126 and the shelf portion 128 of the inserter 104. It can also be seen in FIG. 3A that the inner driver 122, which has been inserted into the plug 110, defines a taper 130, as further described below. After the suture anchor assembly 100 is loaded with one or more sutures 10, the sutures are grossly tensioned and the suture anchor assembly 100 is fully pounded into bone.

As shown in FIG. 3B, with the suture anchor assembly 100 fully implanted into bone, the inner driver 122 is actuated by the handle (not shown) to descend the plug 110 both axially and rotationally within the cannulation 114 of the tip 106, thus trapping the suture 10 between the distal end of the plug 110 and the distal end of the cannulation 114. Advantageously, this provides enhanced suture retention force within the suture anchor assembly 100, causing the suture 10 to remain in place within the bone. Additionally, the bone surrounding the suture anchor assembly 100, as well as the suture tension on the tip 106, work to keep the tip 106 in place at the distal end of the anchor body 108. Since the plug 110 is now fully threaded into the cannulation 114 of the tip 106, the inserter 104 can be disengaged from the suture anchor assembly 100, leaving behind the anchor body 108, the plug 110 and the tip 106 holding the suture 10.

Figure 3C:
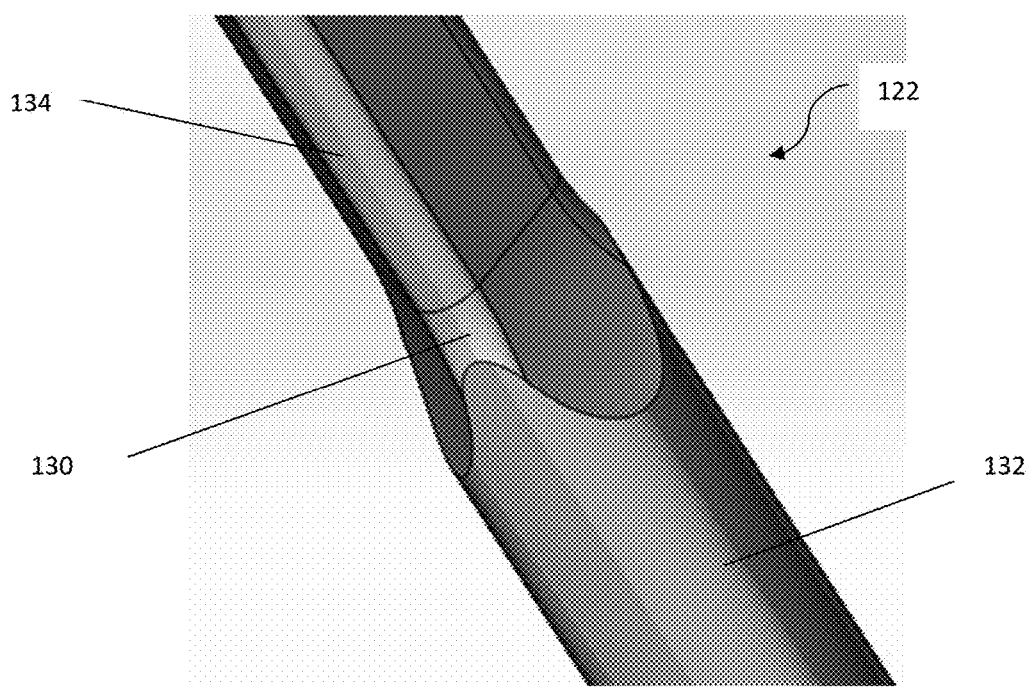
FIG. 3C is a detailed view of the transition region between the circular and polygonal portions of the inner driver of FIG. 1A.

FIG. 3C is a detailed illustration of the tapered portion 130 of the inner shaft 122. As can be seen in FIG. 3C, the taper 130 occurs as a transition is made from a round proximal portion 132 to a triangular distal portion 134, which is inserted into the plug 110. It is also contemplated by this disclosure that the distal portion 134 could be formed in the shape of any polygon other than a triangle. Thus, the interior of the plug 110 has a configuration to match the distal portion 134 of the inner shaft 122. A polygonal configuration is advantageous for yielding a net higher torque capability than a cylindrical driver.

In other examples of the suture anchor assembly 100, not shown, it is contemplated that the plug 110 could connect the tip 106 and the inserter 104 with a non-threaded interface, such as a light interference fit. In this case, the plug 110, the cannulation 114 of the tip 106, and the inner shaft cannulation 124 of the inserter 104 would not be limited to a cylindrical formation, but could be, for example, a square, hexagon or other polygon. Such a configuration would be useful in the miniaturization of the suture anchor assembly 100.

Although the present disclosure has been described with respect to various examples, it would be apparent to one of ordinary skill in the art that various other examples are possible, without departing from the spirit and scope as defined in the appended claims.

The invention claimed is:

1. A suture anchor assembly, comprising:
an anchor, comprising:
   a tip comprising:
      a cylindrical proximal portion and a tapered distal portion, an eyelet extending transversely through the proximal portion dimensioned to receive one or more sutures; and
      a cannulation formed within the proximal portion in communication with the eyelet, the cannulation having threads extending from a proximal end of the cannulation to at least a region within the eyelet;
   an elongated anchor body formed separately from the tip, the anchor body comprising an open cannula extending from a proximal end to a distal end, the distal end of the cannula dimensioned to receive substantially an entirety of the proximal portion of the tip, including the eyelet; and
   a threaded plug formed separately from both the anchor body and the tip, the plug configured to engage the cannulation of the tip; and
an inserter comprising:
   an outer shaft dimensioned for receipt within the cannula of the anchor body, an inner surface of a cannulation of the outer shaft comprising threads engageable with the threads of the plug; and
   an inner shaft dimensioned for receipt within the outer shaft, the inner shaft being axially and rotationally moveable independent of the outer shaft for descending the plug within the cannulation of the tip.

2. The suture anchor assembly of claim 1, wherein the tip is comprised of a material selected to be harder than a material of the anchor body.

3. The suture anchor assembly of claim 1, wherein the tip is comprised of one of plastic, titanium and stainless steel.

4. The suture anchor assembly of claim 1, wherein the anchor body is comprised of a bioabsorbable material.

5. The suture anchor assembly of claim 1, wherein a transverse anchor body eyelet is located on the anchor body such that, when the proximal portion of the tip is inserted into the distal end of the cannula of the anchor body, the tip eyelet and the anchor body eyelet are aligned.

6. The suture anchor assembly of claim 5, further comprising a suture extending transversely through the tip eyelet and the anchor body eyelet.

7. The suture anchor assembly of claim 1, wherein the inner shaft of the inserter is configured for insertion into the plug.

8. The suture anchor assembly of claim 1, wherein the anchor body is trapped axially between the inserter and the tip when the threaded plug is engaged with the threaded cannulation of the outer shaft of the inserter and the threaded cannulation of the tip.

9. The suture anchor assembly of claim 1, wherein the interface between the inserter and the anchor body is a slip fit.

10. The suture anchor assembly of claim 1, wherein the interface between the anchor body and the tip is a slip fit.

11. The suture anchor assembly of claim 1, wherein the plug is comprised of one of a polymer, a plastic and a metal.

12. The suture anchor assembly of claim 1, wherein a diameter of the plug is about 2 mm.

13. The suture anchor assembly of claim 1, wherein a length of the plug is about 5.25 mm.

14. The suture anchor assembly of claim 1, wherein the anchor body comprises surface features to aid in the retention in bone.

15. The suture anchor assembly of claim 1, wherein the inner shaft of the inserter defines a taper between a round proximal portion and a polygonal distal portion.

16. The suture anchor assembly of claim 15, wherein the polygonal distal portion of the inner shaft is triangular.

17. The suture anchor assembly of claim 1, wherein the anchor body is tapered toward the tip, such that a diameter of a proximal-most end of the distal portion of the tip does not extend beyond a diameter of a distal-most end of the anchor body.

* * * * *